United States Patent [19]

Omura et al.

[11] 3,974,273

[45] Aug. 10, 1976

[54] COMPOUND NA-337 AND A PROCESS FOR PRODUCING THE SAME BY FERMENTATION

[75] Inventors: Satoshi Omura, Tokyo; Haruo Tanaka, Machida; Juichi Awaya; Yaeko Konda, Tokyo; Yoshitsugu Narimatsu, Hiratsuka; Masayuki Onda, Tokyo, all of Japan

[73] Assignee: The Kitasato Institute, Tokyo, Japan

[22] Filed: Mar. 14, 1975

[21] Appl. No.: 558,573

[30] Foreign Application Priority Data
Apr. 3, 1974 Japan................................ 49-36939

[52] U.S. Cl................................ 424/122; 195/80 R
[51] Int. Cl.$^2$.................... A61K 35/66; C12B 1/00; C12K 1/00

[58] Field of Search..................... 424/122; 195/80 R

[56] References Cited
OTHER PUBLICATIONS
Nara et al.—Chem. Abst. vol. 80 (1974) p. 106,850u.

*Primary Examiner*—Sam Rosen
*Attorney, Agent, or Firm*—Wolder & Gross

[57] ABSTRACT

This invention relates to a new compound NA-337 and a process for producing the same by fermentation. NA-337 is positive in Dragendorff's reagent. NA-337 is confirmed to be a new compound having a fat-clearing activity. This compound is produced by fermentation, in which an NA-337-producing strain is cultured aerobically in a medium and the accumulated NA-337 is recovered from the cultured matters.

7 Claims, 2 Drawing Figures

1

COMPOUND NA-337 AND A PROCESS FOR PRODUCING THE SAME BY FERMENTATION

BACKGROUND OF INVENTION

We have carried out studies on therapeutically active substances produced by actinomycetes, resulting in the discovery that a new compound designated as NA-337 is produced by fermentation of a strain belonging to the genus Streptomyces.

SUMMARY OF INVENTION

The present invention relates to a new compound designated as NA-337 and a process for producing the same by fermentation. As the compound is positive in the reaction with Dragendorff's reagent, it belongs to the class of alkaloids. NA-337 is a novel compound which is expected to be utilized as a pharmaceutical because of its fat-clearing activity.

The hydrochloride of NA-337 has the following physical and chemical characteristics.

1. Elementary analysis

Found: C—64.31%; H—8.71%; N—7.10%; Calculated (as $C_{10}H_{15}N \cdot HCl$): C—64.68%; H—8.68%; N—7.54%

2. Molecular weight m/e of free NA-337 determined by mass spectrum is 149.122. The theoretical value for $C_{10}H_{15}N$ is 149.120.

3. Melting point: 150°C (decomposed).

Figure 1:
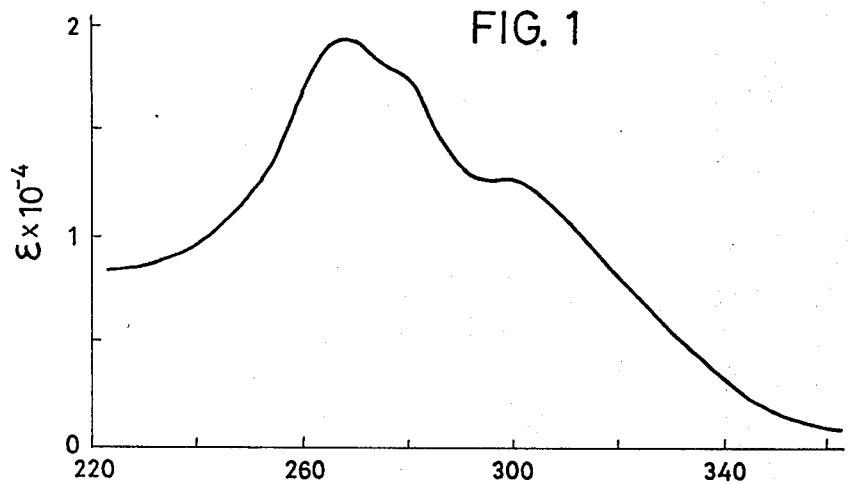

4. Ultraviolet absorption spectra $\lambda_{max}^{MeOH}$ nm($\epsilon$): 267 (19,200); 300 (12,500) (FIG. 1)

5. Infrared absorption spectra

Figure 2:
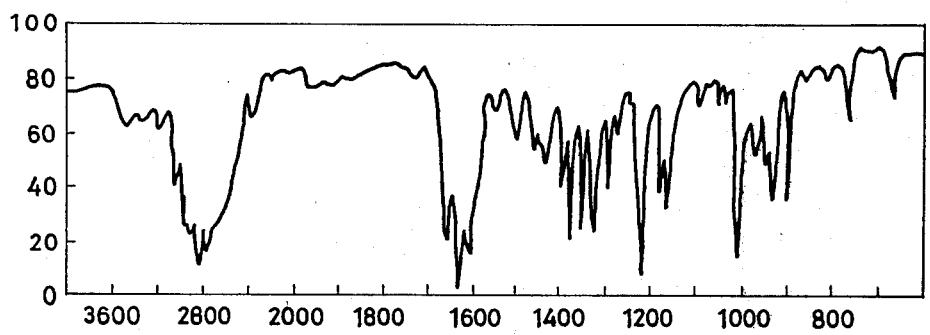

Comparatively strong absorption at 2500–3000, 1650, 1625, 1605, 1383, 1353, 1328, 1300, 1223, 1182, 1166, 1010, 932 and 905 (KBr method). (FIG. 2)

6. Solubility

Easily soluble in water, methanol and ethanol; soluble in chloroform and hardly soluble in benzene and n-hexane.

7. Color reactions

Positive in the reactions with Dragendorff's reagent and platinum chloride-potassium iodide reagent. Negative in the reactions with ninhydrin, anthrone and ferric chloride reagents.

The present invention further provides a process for producing a novel compound NA-337 characterized by culturing aerobically an NA-337 strain belonging to the genus Streptomyces in a medium and recovering the accumulated NA-337 from the cultured matters.

The microbiological characteristics of the above-mentioned NA-337 strain having the ability of producing the novel alkaloid NA-337 are as follows.

I. Morphological Characteristics:

Forming abundantly aerial mycelium on synthetic agar medium and protein containing medium. Spores borne on verticillate sporophore. Spores in a chain and size of $0.4\mu \times 0.8\mu$ (stab), smooth surface. Flagellum spore and sporangium not formed.

II. Characteristics on Various Media:

| Media | Growth | Reverse | Aerial Mycelium | Soluble Pigment |
|---|---|---|---|---|
| sucrose-nitrate agar | moderate; colorless | creamy | bright yellow | pale yellow |
| glucose-nitrate agar | moderate; colorless | yellowish brown | yellowish white | pale yellow |
| glucose asparagine agar | good; colorless | yellowish brown | yellowish white | pale yellow |
| glycerol-asparagine agar | good; colorless | yellowish brown | pale yellow | grayish brown |
| starch-inorganic salts agar | good; colorless | pale brown | pale yellow | none |
| tyrosine agar | good; colorless | pale yellow | yellowish white | none |
| nutrient agar | moderate; colorless | pale yellowish brown | white | pale yellow |
| yeast extract-molt agar | good; colorless | reddish yellow | pale yellow | reddish yellow |
| oat meal agar | good; colorless | pale olive | none | pale yellow |
| peptone-yeast extract-iron agar | good; colorless | yellowish brown | pale olive | black |
| glucose-peptone agar | moderate; colorless | brown | yellowish brown | reddish brown |
| glucose gelatin | poor | — | reddish brown | dark brown |
| skim milk | grow on liquid surface; creamy | — | white | yellowish brown |

Note:
20°C for glucose-gelatin medium
38°C for skim milk medium
27°C for other media

III. Physiological Characteristics

1. Growth temperature: 10°–45°C
2. Formation of melanoid pigment:
   a. tryptone-yeast extract liquid: positive
   b. peptone-yeast extract-iron agar: positive
   c. tyrosine agar: negative
3. Hydrolization of starch: positive
4. Formation of hydrogen sulfide: positive
5. Solubilization of gelatin: positive
6. Peptonization of skim milk: positive
7. Coagulation of skim milk: positive
8. Decomposition of cellulose: positive (very weak)

IV. Utilization of Various Carbon Sources (on Pridham-Gottlieb agar media)

D-glucose, D-fructose, inositol, L-rhamnose, D-mannitol, maltose, mannose, galactose, glycerol and starch are utilized. Arabinose, D-xylose, sucrose and raffinose are not used.

From the above-mentioned microbiological characteristics, it has been concluded that the NA-337 strain belongs to the Verticillate group of the genus Streptomyces described in "Applied Microbiology", Vol. 6, Page 52 (1958). A preferable NA-337 strain has been deposited with the Fermentation Research Institute, Agency of Industrial Science and Technology and assigned an accession number of FERM 2515.

Strains which may be used in the present invention include not only the above-mentioned NA-337 strain and mutants derived therefrom but also any strain belonging to the genus Streptomyces and capable of producing new compound NA-337.

As a medium used for the present invention, either synthetic or organic medium may be used when it contains carbon source, nitrogen source, inorganic materials and, if desired, other nutrients. The medium is adjusted to a pH of 6–10 in use.

Any kind of carbon and nitrogen sources may be used when it is adaptable for the used strain. As a carbon source, for example, carbohydrates such as glucose, glycerol, fructose, sucrose, mannose, maltose, mannitol, galactose, lactose, ribose, starch, starch hydrolyzate and mollasses, etc. may be used. The concentration of carbon source is preferably 0.5–5.0% (calculated as glucose) based on the medium. Furthermore, various organic acids such as gluconic acid, pyruvic acid, lactic acid and acetic acid, etc., various amino acids such as glycine, glutamic acid and alanine, etc. and other various organic compounds such as glutamine and like may be used.

As a nitrogen source, ammonia; various organic and inorganic ammonium salts such as ammonium chloride, ammonium phosphate, ammonium sulfate, ammonium nitrate, etc.; urea; nitrogen-containing materials such as peptone, NZ-amine, meat extract, dried yeast, yeast extract, corn steep liquor, casein hydrolyzate, fish meal, digested fish meal, soybean meal, digested soybean meal, defatted-soybean meal, digested defatted-soybean meal, pupa hydrolyzate, etc.; various amino acids such as glycine, glutamic acid, alanine, etc.; and other materials may be used.

As an inorganic substance, potassium monohydrogen phosphate, potassium dihydrogen phosphate, magnesium sulfate etc. may be used. Furthermore, it is possible to use a trace amount of heavy metal salts, but it is not always necessary to use them when culture medium in use contains natural substance.

Fermentation is carried out under an aerobic condition by shaking cultivation, submerged cultivation with aeration and agitation, etc. The culture temperature is usually within a range of from 15° to 40°C and the culture period is usually from 1 to 7 days. A large amount of NA-337 is produced and accumulated in both the medium and microbial body.

After completion of culturing, compound NA-337 is recovered from the cultured matters. For example, the cultured matters are separated into microbial body and filtrate. The filtrate is adjusted to an alkaline pH and is subjected to a recovery of compound NA-337 by a known method used conventionally for the extraction and purification of alkaloid.

PREFERRED EMBODIMENT

With reference to FIGS. 1 and 2 showing UV and IR absorption spectra of NA-337 respectively, the following nonlimitative example illustrates the invention.

EXAMPLE

A liquid medium containing 2% of glucose, 0.5% of peptone, 0.5% of meat extract, 0.3% of dried yeast, 0.5% of sodium chloride and 0.3% of calcium carbonate was prepared and adjusted to pH of 7.0 with caustic soda. Each 125 ml of the medium was put in a 500 ml Sakaguchi flask and sterilized. One loop of NA-337 strain was inoculated to the medium and cultured at 27°C for 2 days with shaking. The culture was used as a seed culture.

20 ml of the medium having the same composition as that of the medium used for said seed culture was placed in a 30-liter jar fermenter and then sterilized. The above-mentioned seed culture was inoculated to the medium at a ratio of 1% (volume) and then cultured at 27°C for 1 day with aeration and agitation. The culture was used as a second seed. 200 liters of the same medium was placed in a 400-liter fermenter and sterilized. The second seed was inoculated to the medium at a ratio of 10% (volume) and cultured at 27°C for 2 days with aeration and agitation.

The microbial body was removed off from the resultant fermented liquor by filtration. The filtrate was adjusted to a pH more than 10 with aqueous ammonia and subjected to an extraction with butylacetate. The butyl acetate layer was subjected to an extraction with 0.1N hydrochloric acid. The 0.1N hydrochloric acid extract was adjusted to a pH more than 10 with aqueous ammonia and subjected to an extraction with ethylether. The ethylether layer was dehydrated with anhydrous sodium sulfate and concentrated under a reduced pressure, and then added with ethylether saturated with picric acid to obtain picrate of the compound NA-337 (yellow precipitate). The chloroform-soluble fraction of the precipitate was recrystallized to obtain 6.65 g of yellow crystals.

The crystals obtained were dissolved in chloroform and then added with caustic soda. After washing the chloroform layer with water, hydrogen chloride gas was passed through the layer. By adding gradually ether to the layer, white crystals of hydrochloride of NA-377 were obtained with a yield of 2.21g.

What is claimed is:

1. A new compound having the following characteristics as hydrochloride:

Elementary analysis:

Found: C - 64.31%
H - 8.71%
N - 7.10%

Calculated (as $C_{10}H_{15}N \cdot HCl$): C - 64.68%
H - 8.68%
N - 7.54%

Molecular weight:

m/e of free NA-337 determined by mass spectrum — 149.122 Theoretical value for $C_{10}H_{15}N$ — 149.120

Melting point: 150°C (decomposed)

Ultraviolet absorption spectra $\lambda_{max}^{MeOH}$ nm($\epsilon$): 267 (19,000); 300 (12,500)

Infrared absorption spectra

Comparatively strong absorption at 2500–3000, 1650, 1625, 1605, 1383, 1353, 1328, 1300, 1223, 1182, 1166, 1010, 932 and 905 when measured by KBr method.

Solubility

Easily soluble in water, methanol and ethanol; soluble in chloroform and hardly soluble in benzene and n-hexane.

Color reactions:

Positive in the reactions with Dragendorff's reagent and platinum chloride-potassium iodide reagent;

negative in the reactions with ninhydrin, anthrone and ferric chloride reagents.

2. A process for producing a new compound according to claim 1 by fermentation comprising the steps of culturing aerobically an NA-337 producing microorganism belonging to the verticillate group of the genus Streptomyces in a medium and recovering the accumulated NA-337 from the cultured medium.

3. A process of claim 2, in which the strain is Streptomyces sp. NA-337 (FERM-P No. 2515).

4. A process of claim 2, in which the medium contains carbon sources, nitrogen sources and inorganic materials.

5. A process of claim 4, in which the medium is adjusted to a pH of from 6 to 10.

6. A process of claim 2, in which the culturing is carried out at a temperature of from 15° to 40°C.

7. A process of claim 2, in which the accumulated NA-337 is recovered from the medium and microbial bodies.

* * * * *